(12) United States Patent
Krantz et al.

(10) Patent No.: US 7,780,600 B2
(45) Date of Patent: *Aug. 24, 2010

(54) SYSTEM AND METHOD FOR UTILIZING SHAPE ANALYSIS TO ASSESS FETAL ABNORMALITY

(75) Inventors: David A. Krantz, Bayside, NY (US); Francesco Orlandi, Palermo (IT)

(73) Assignee: NTD Laboratories, Inc., Melville, NY (US)

( * ) Notice: Subject to any disclaimer, the term of this patent is extended or adjusted under 35 U.S.C. 154(b) by 244 days.

This patent is subject to a terminal disclaimer.

(21) Appl. No.: 11/879,258

(22) Filed: Jul. 17, 2007

(65) Prior Publication Data

US 2008/0077014 A1    Mar. 27, 2008

Related U.S. Application Data

(63) Continuation of application No. 10/808,347, filed on Mar. 25, 2004, now Pat. No. 7,244,233.

(60) Provisional application No. 60/490,540, filed on Jul. 29, 2003, provisional application No. 60/493,442, filed on Aug. 8, 2003.

(51) Int. Cl.
*A61B 8/00* (2006.01)

(52) U.S. Cl. .................. 600/443; 382/199

(58) Field of Classification Search ............. 600/437, 600/440, 443, 448, 458; 128/916; 382/128, 382/131, 173, 190, 194, 195, 203, 206, 217, 382/224, 256, 266
See application file for complete search history.

(56) References Cited

U.S. PATENT DOCUMENTS

| 5,235,981 | A  | 8/1993  | Hascoet et al.  |
|-----------|----|---------|-----------------|
| 5,252,489 | A  | 10/1993 | Macri           |
| 5,588,435 | A  | 12/1996 | Weng et al.     |
| 5,622,176 | A  | 4/1997  | Vintzileos et al. |
| 5,740,266 | A  | 4/1998  | Weiss et al.    |
| 5,797,396 | A  | 8/1998  | Geiser et al.   |
| 5,898,797 | A  | 4/1999  | Weiss et al.    |
| 6,048,314 | A  | 4/2000  | Nikom           |
| 6,306,089 | B1 | 10/2001 | Coleman et al.  |
| 6,573,103 | B1 | 6/2003  | Wald            |
| 6,585,647 | B1 | 7/2003  | Winder          |

(Continued)

FOREIGN PATENT DOCUMENTS

WO    WO-94/14132 A1    6/1994

OTHER PUBLICATIONS

Kanokwan Tangchaitrong, et al., "Fourier Analysis of Facial Profiles of Young Twins", American Journal of Physical Anthroplogy 113, 2000pp. 369-379.

(Continued)

*Primary Examiner*—Ruth S Smith
*Assistant Examiner*—Christopher Cook
(74) *Attorney, Agent, or Firm*—Daniel P. Burke & Associates, PLLC.

(57) ABSTRACT

A method and system for utilizing shape analysis to assess fetal abnormality. According to one embodiment, coordinates of points identifying a shape in a fetal image are received, coefficients of one or more mathematical functions that describe the identified shape are determined, and the determined coefficients are utilized as markers to assess fetal abnormality.

36 Claims, 12 Drawing Sheets

U.S. PATENT DOCUMENTS

| | | | |
|---|---|---|---|
| 6,695,780 | B1 | 2/2004 | Nahum et al. |
| 6,836,557 | B2 | 12/2004 | Tamez-Pena et al. |
| 6,939,301 | B2 | 9/2005 | Abdelhak |
| 7,244,233 | B2 | 7/2007 | Krantz et al. |
| 2002/0133075 | A1 | 9/2002 | Abdelhak |

OTHER PUBLICATIONS

Pete E. Lestrel, et al. "Fourier Analysis of the Cranium in Trisomy 21", Aug. 10, 1975, pp. 385-398.

Annabelle Azancot, M.D., et al "Analysis of Ventricular Shape by Echocardiography in normal fetus, newborns and infants" vol. 68, No. 6, Dec. 1983, pp. 1201-1211.

Irwin R. Merkatz, M.D., et al., "An association between low material serum a-fetoprotein and fetal chromosomal abnormalities", vol. 48, No. 7, Apr. 1, 1984, pp. 886-894.

C. Lockwood, M.D., et al., "A sonographic screening method for Down Syndrome", Oct. 1987, pp. 803-808.

J.E. Allanson, et al., "Anthropometric Craniofacial Pattern Profiles in Down Syndrome", 1993, Wiley-Liss, Inc., American Journal of Medical Genetics 47, pp. 748-752.

Noelle Stempfle, et al., "Skeletal abnormalities in fetuses with Down's Syndrome: A radiographic Post-Mortem Study", Pediatric Radiol, 1999, pp. 682-687.

George Stetten, et al., "Real-Time Three-Dimensional Ultrasound Methods for Shape Analysis and Visualization", 2001, pp. 221-230.

Leslie G. Farkas, M.D., "Surface Anatomy of the Face in Down's Syndrome: Age-Related Changes of Anthropometric Proportion Indices in the Craniofacial Regions", The Journal of Craniofacial Surgery, vol. 13, No. 3, May 2002, pp. 368-374.

Jeffrey, Nathan, et al, "Ossification and Midline Shape Changes of the Human Fetal Cranial Base", American Journal of Physical Anthropology, 123:78-90, Wiley-Liss, Inc.,2004.

J.N. Parnell, et al. "A computer program for comparing irregular two-dimensional forms", Computer Programs in Biomedicine, Amsterdam, NL, vol. 7, No. 3, Sep. 1, 1977, pp. 145-161.

D.R. Johnson, et al. "Measurement of biological shape: a general method applied to mouse vertebrae", Journal of Embryology and Experimental Morphology, vol. 90, Dec. 1985, pp. 363-377.

K. Spencer, et al. "Short communication screening for trisomy 13 by fetal nuchal translucency and maternal serum free beta HCG and PAPP-A at 10-14 weeks gestation",Prenatal Diagnosis,Chichester, Sussex, GB,vol. 26,May 1, 2000 pp. 411-416.

Pete Lestrel "Method for analyzing complex two-dimensional forms: elliptical Fourier functions", American Journal of Human Biology, vol. 1, 1989, pp. 149-164.

Krantz,et al. "Geometric morphometric analysis of shape outlines of the normal and abnormal fetal skull using three-dimensional sonographic multiplanar display", Ultrasound Obstet Gynecol, vol. 27, 2006 pp. 167-172.

F.L. Bookstein "Shape and the information in medical images: a decade of the morphometric synthesis", Computer Vision and Image Understanding, Academic Press,U S vol. 66, No. 2, May 1, 1997, pp. 97-118.

M.B. McNay, et al."Forty years of obstetric ultrasound 1957-1997:from A-scope to three dimensions-a five year experience", Ultrasound in Medicine and Biology, New York, U.S.,vol. 25, No. 1,Jan. 1, 1999,pp. 3-56.

Pete E. Lestrel, et al., "Fourier Analysis of the Cranium in Trisomy 21", Growth, Aug. 10, 1976, pp. 385-398.

Michiel C. Van Den Hof, MD et al., "Evaluation of the lemon and banana signs in one hundred thirty fetuses with open spina bifida", Am. J. Obstet. Gynecol., Feb. 1990, pp. 322-327, vol. 162, No. 2.

Help Screen from NTSYSPC, Version 2.1, Fourier Analysis, 2000.

SYSTEM AND METHOD FOR UTILIZING SHAPE ANALYSIS TO ASSESS FETAL ABNORMALITY

CROSS REFERENCE TO RELATED APPLICATIONS

This application is a continuation of U.S. patent application Ser. No. 10/808,347 filed on Mar. 25, 2004, now U.S. Pat. No. 7,244,233. This application claims the benefit under 35 U.S.C. §119(e) of U.S. Provisional Application No. 60/490,540, filed Jul. 29, 2003 and U.S. Provisional Application No. 60/493,442, filed Aug. 8, 2003, both of which are hereby incorporated by reference as if repeated herein in their entirety.

BACKGROUND OF THE INVENTION

Prenatal screening methods are routinely employed to assess the likelihood of fetal abnormalities, commonly referred to as birth defects. For example, Down syndrome or Trisomy 21 is the most common cause of severe learning disability and accounts for approximately one half of all chromosomal anomalies in live born children.

Current methods to screen prenatally for Trisomy 21 involve maternal serum testing for biochemical markers and/or ultrasound evaluation of biophysical markers. Maternal serum screening involves the quantitative analysis of biochemical markers and risk assessment based on likelihood ratios derived from the population distributions of affected and unaffected pregnancies. Ultrasound evaluation, however, has historically involved visual observation of a fetal image and deciding empirically whether the image looks "normal" or "abnormal" (for example, whether the cerebellum appears as a banana sign for open Spina Bifida). This approach requires extensive experience in the "art" of ultrasound and the interpretation is necessarily subjective.

Accordingly, there is a need in the art for a system and method that adequately evaluates the morphological changes observed with birth defects during prenatal screening.

SUMMARY OF THE INVENTION

Embodiments of the present invention provide for utilizing shape analysis to assess fetal abnormality. According to one embodiment, coordinates of points identifying a shape in a fetal image are received, coefficients of one or more mathematical functions that describe the identified shape are determined, and the determined coefficients are utilized as markers to assess fetal abnormality.

DETAILED DESCRIPTION

Overview

Figure 1:
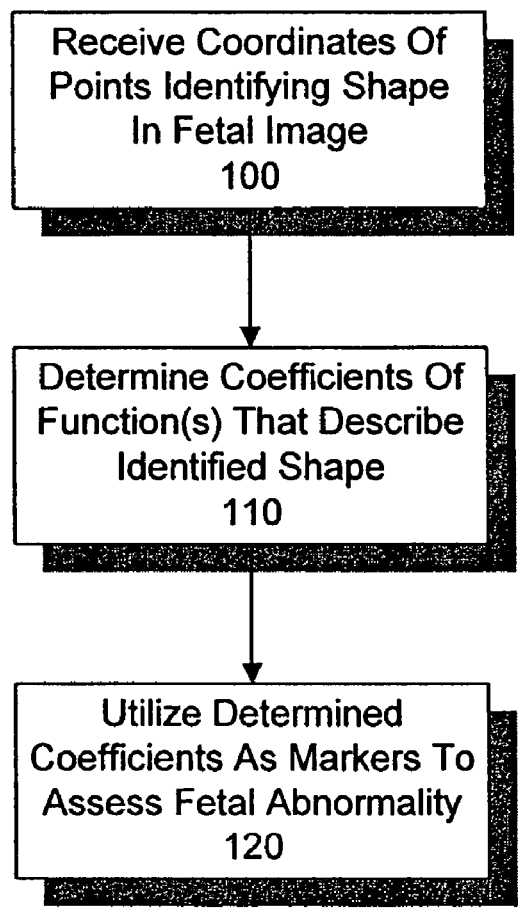
FIG. 1 is a flow chart that depicts a process for utilizing shape analysis to assess fetal abnormality in accordance with an embodiment of the present invention.

FIG. 1 depicts a process for utilizing shape analysis to assess fetal abnormality in accordance with an embodiment of the present invention. Upon receiving coordinates of points identifying a shape in a fetal image (step 100), the coordinates are used to determine coefficients of a mathematical function or functions that describe the identified shape (step 110). These coefficients are used as markers to assess fetal abnormality (step 120).

Figure 2:
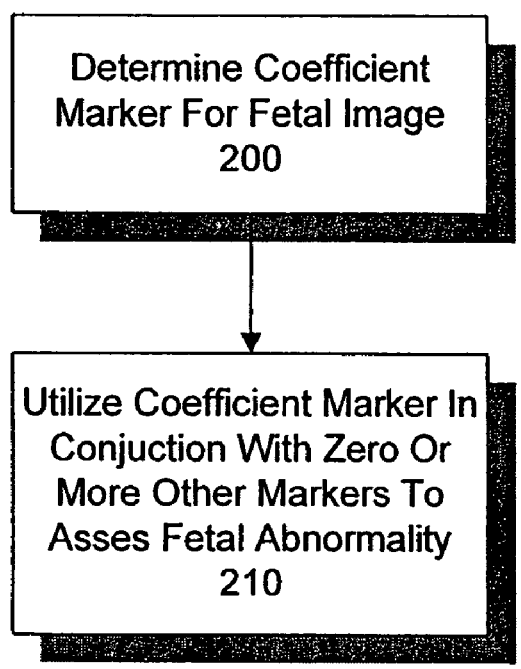
FIG. 2 is a flow chart that depicts a process for utilizing shape analysis to assess fetal abnormality in accordance with an embodiment of the present invention.

As shown in FIG. 2, once the coefficient markers are determined (step 200), they may be used by themselves or with other markers to assess fetal abnormality (step 210). A fetal abnormality may be assessed by comparing a patient's coefficient markers to reference data of coefficient markers by conducting a statistical analysis. The reference data may contain unaffected patients and/or affected patients. The statistical comparison could result in a risk of fetal abnormality, a likelihood ratio for a fetal abnormality or an index value that could be considered within range or outside of range for a fetal abnormality.

The use of multidimensional coordinates allows for the evaluation of a shape as a whole. In one embodiment, a statistical shape analysis involves the tracing of an outline around the part of a fetal image to be analyzed. The points that make up this curve are then analyzed to derive a function that best fits the individualized points around the outline. The coefficients of this function may be considered random variables and can be determined for each evaluated image. The coefficients may then be analyzed using multivariate statistics to determine if they are outliers compared to the normal population. A subject shape that has coefficients outside the normal ranges observed in control shapes would indicate that the subject shape was significantly different than expected.

Described below are several embodiments within which the present invention may be implemented.

Architecture

Figure 3:
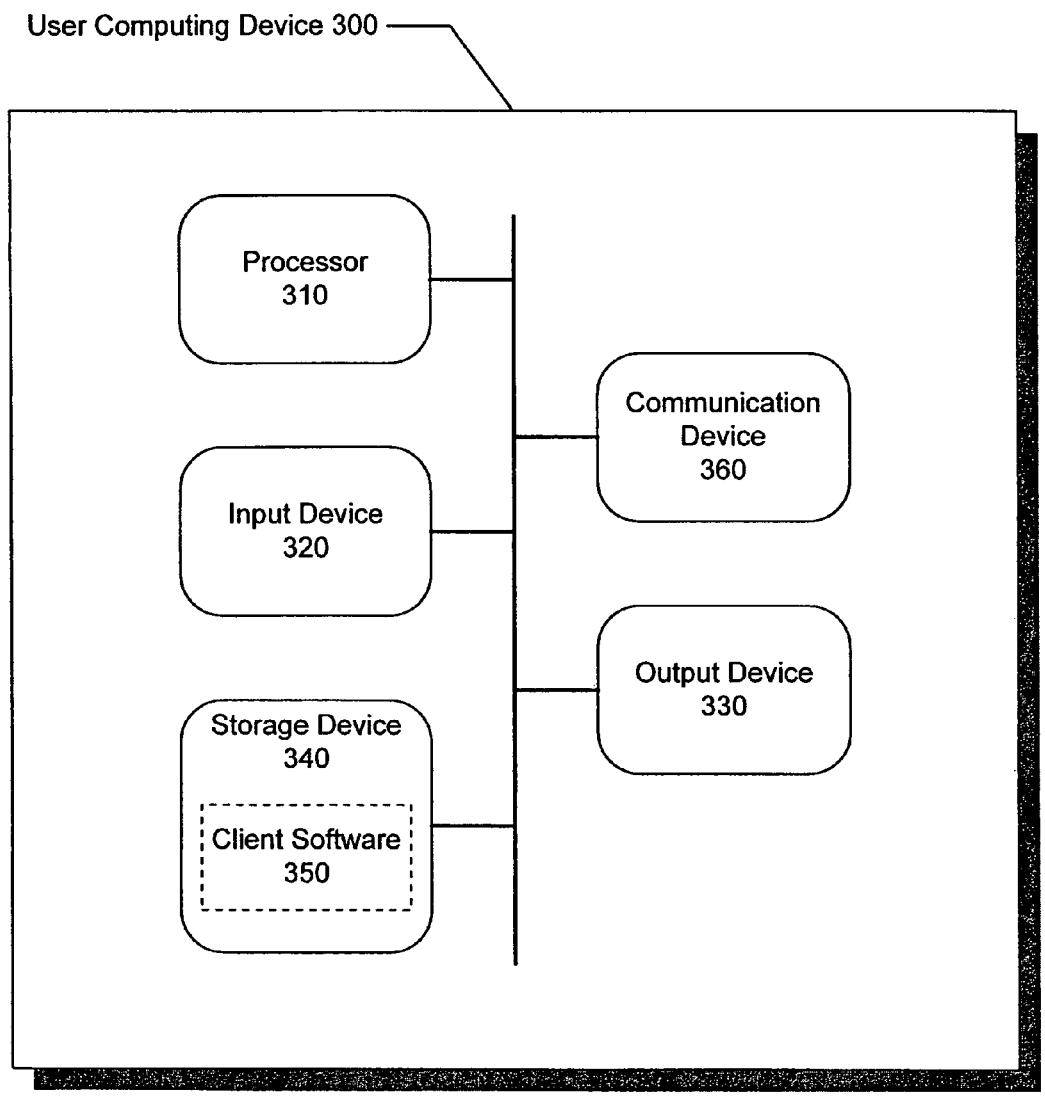
FIG. 3 is a block diagram that depicts a user computing device in accordance with an embodiment of the present invention.
Figure 4:
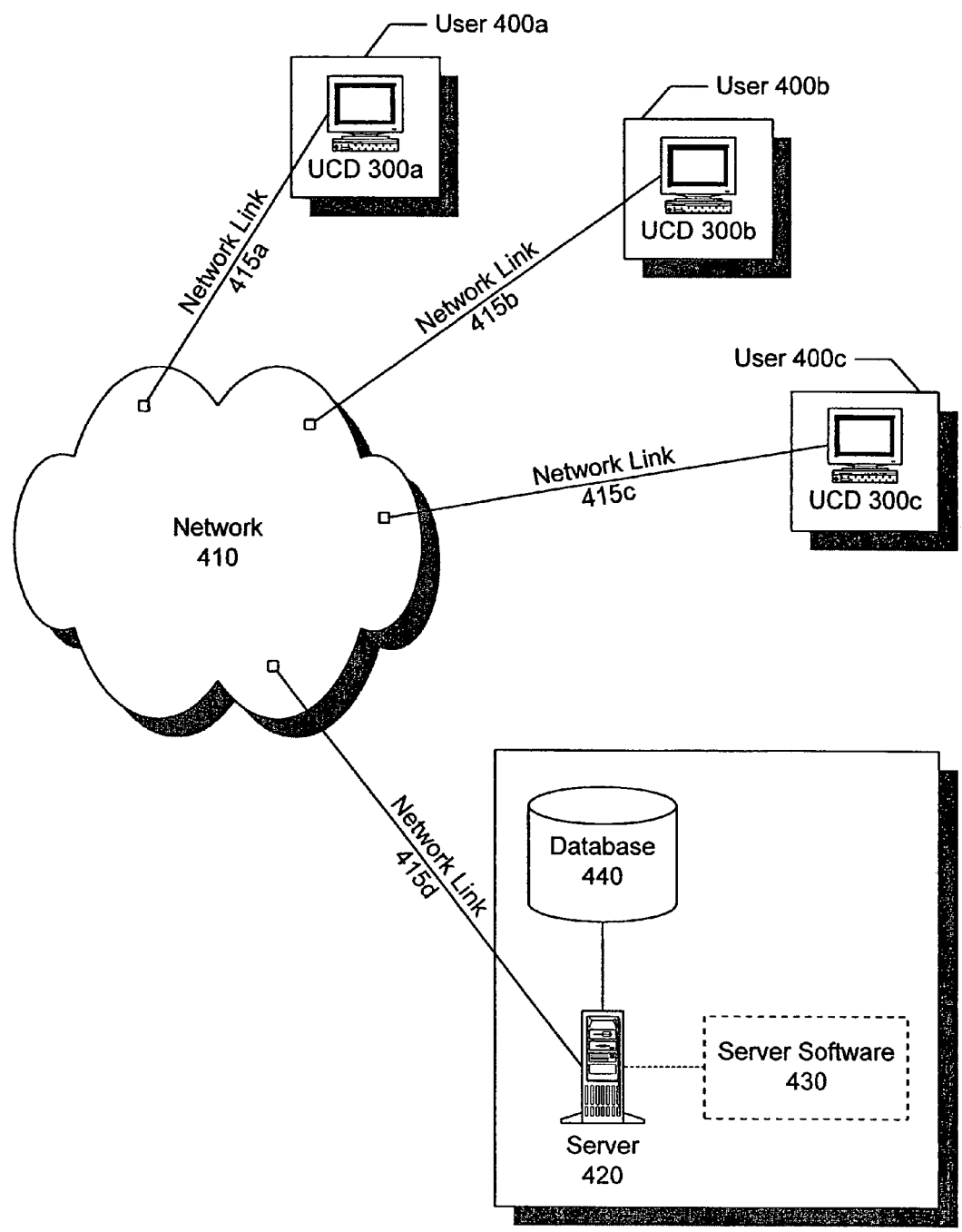
FIG. 4 is a block diagram that depicts a network architecture in accordance with an embodiment of the present invention.

FIGS. 3 and 4 illustrate the components of a basic computer and network architecture in accordance with an embodiment of the present invention. FIG. 3 depicts user computing device 300, which may be an ultrasound machine (3-D, 4-D or color), MRI or CAT scan machine, fetoscopy machine, workstation, personal computer, handheld personal digital assistant ("PDA"), or any other type of microprocessor-based device. User computing device 300 may include a processor 310, input device 320, output device 330, storage device 340, client software 350, and communication device 360.

Input device 320 may include a keyboard, mouse, pen-operated touch screen or monitor, voice-recognition device, or any other device that accepts input. Output device 330 may include a monitor, printer, disk drive, speakers, or any other device that provides output.

Storage device 340 may include volatile and nonvolatile data storage, including one or more electrical, magnetic or optical memories such as a RAM, cache, hard drive, CD-ROM drive, tape drive or removable storage disk. Communication device 360 may include a modem, network interface card, or any other device capable of transmitting and receiving signals over a network. The components of user computing device 300 may be connected via an electrical bus or wirelessly.

Client software 350 may be stored in storage device 340 and executed by processor 310, and may include, for example, imaging and analysis software that embodies the functionality of the present invention.

FIG. 4 illustrates a network architecture in accordance with an embodiment of the present invention. The network architecture allows the imaging and analysis functionality of the present invention to be implemented on more than one user computing device 300. For example, in one embodiment user computing device 300 may be an ultrasound machine that performs all of the imaging and analysis functionality of the present invention. In another embodiment, user computing device 300a may be an ultrasound machine that performs the imaging functionality of the present invention, and then transfers image or coordinate data over network 410 to server 420 or user computing device 300b or 300c for analysis of the data. The analyzed data could further be transferred to another user computing device 300 belonging to the patient or another medical services provider for testing with others markers.

Network link 415 may include telephone lines, DSL, cable networks, T1 or T3 lines, wireless network connections, or any other arrangement that implements the transmission and reception of network signals. Network 410 may include any type of interconnected communication system, and may implement any communications protocol, which may secured by any security protocol.

Server 420 includes a processor and memory for executing program instructions, as well as a network interface, and may include a collection of servers. In one particular embodiment, server 420 may include a combination of servers such as an application server and a database server. Database 440 may represent a relational or object database, and may be accessed via server 420.

User computing device 300 and server 420 may implement any operating system, such as Windows or UNIX. Client software 350 and server software 430 may be written in any programming language, such as ABAP, C, C++, Java or Visual Basic.

Analysis of Fetal Head Shape Embodiment

Figure 5:
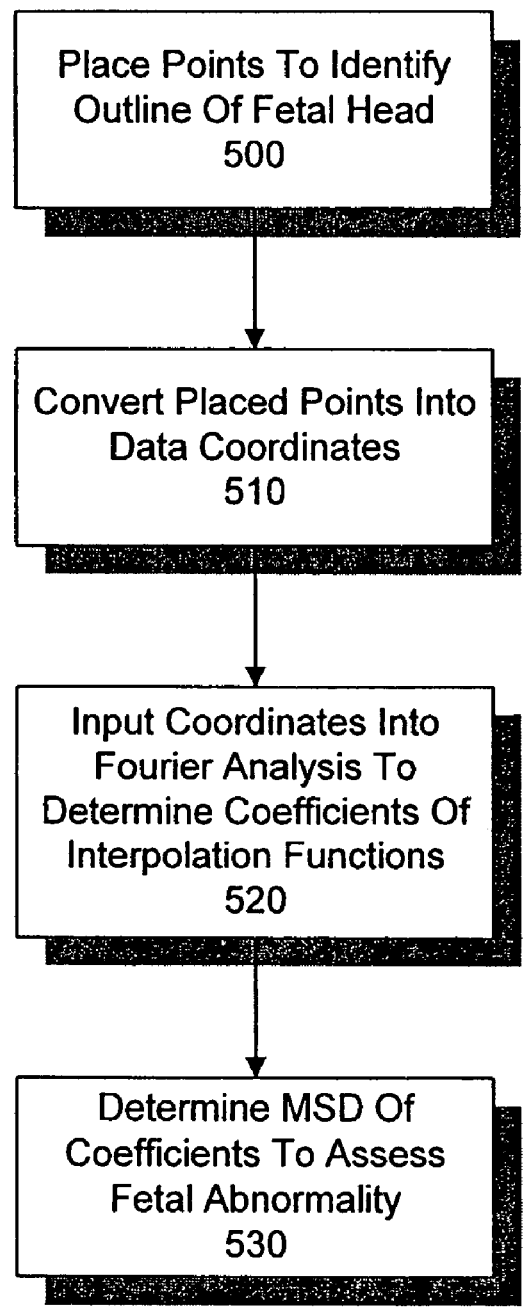
FIG. 5 is a flow chart that depicts a process for utilizing shape analysis of a fetal head to determine risk of fetal abnormality in accordance with an embodiment of the present invention.

FIG. 5 provides an example embodiment of the present invention in which the shape of a fetal head is analyzed to assess fetal abnormality. Fetal abnormalities identifiable through the use of the present invention may include, among others, Down syndrome, Spina Bifida, Trisomy 18, Trisomy 13, frontal bossing, unbalanced translocation, other chromosomal abnormalities, heart abnormalities and abnormalities of any major body organ, structural abnormalities and craniofacial abnormalities.

According to this embodiment, a transverse view of the fetal head is obtained by ultrasound (e.g., UCD 300a), saved as a bit-map image and transferred to another computer (e.g., UCD 300b). Then, in step 500, a user (e.g., user 400b) employs digitizing software (e.g., client software 350), such as TPSDIG, DigitX, CalExcel; DSDigit, Digical, Windig or MacMorph, to create an outline of the fetal head to be analyzed. (Digitizing software provides coordinate data when a user clicks on a particular point in a bit-map image.) In creating the outline, the user may identify two landmarks on the bit-map image along the OFD (ocipito-frontal diameter) axis so that the image may be aligned against a consistent axis and to allow for a uniform assessment of points on each image.

Figure 6:
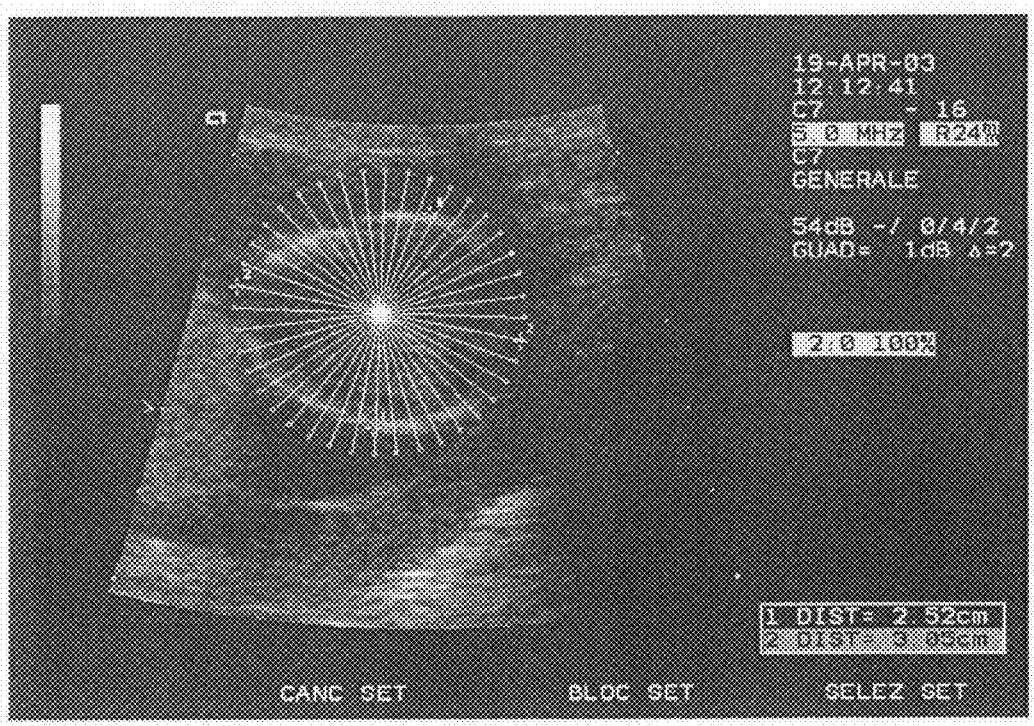
FIG. 6 is a screen shot that depicts outlining of a fetal head in accordance with an embodiment of the present invention.
Figure 7:
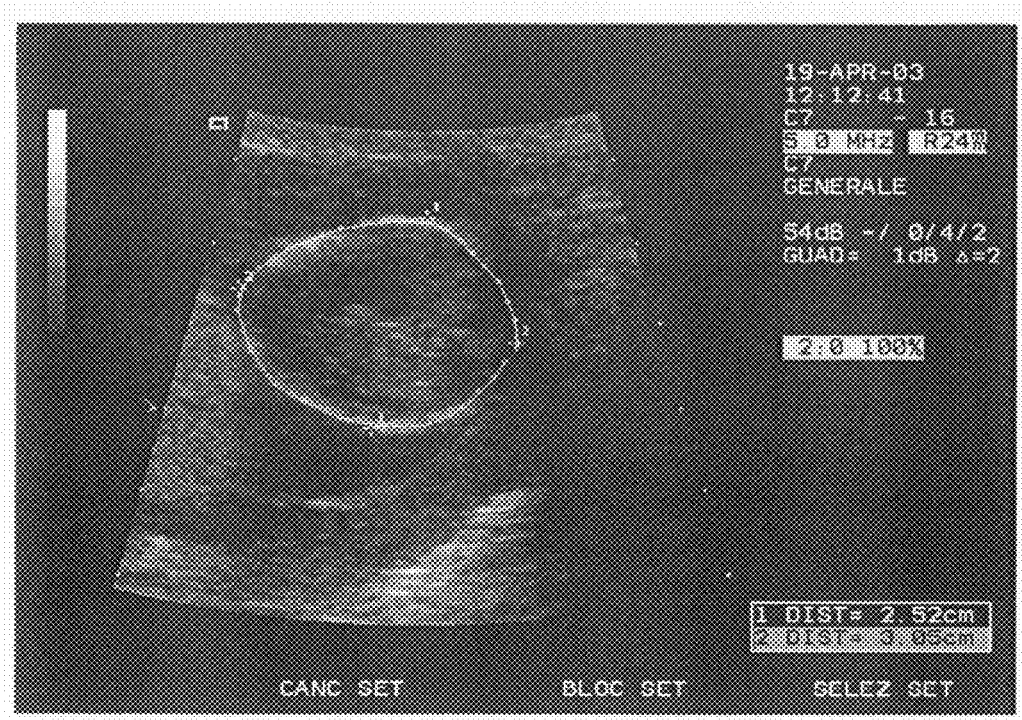
FIG. 7 is a screen shot that depicts outlining of a fetal head in accordance with an embodiment of the present invention.

As shown in FIG. 6, prior to placing the coordinates on the outline, a series of 20 lines, each the length of the OFD axis, may be generated utilizing software employing general algorithms. The first line overlays the OFD axis; the remaining lines are centered at the mid-point of the first line and then are rotated at 9 degrees from the previous line in a counterclockwise manner. Once this "fan" is drawn, the user may place points, via the digitizing software, on the outline of the fetal head where it crosses the equidistant lines of the fan. FIG. 7 shows the resulting 40 points representing the outline. Each small circle connected in the loop represents a point on the image clicked by the user to identify the outline, and the two cross-hair symbols next to the number "2"s represent the OFD positioning landmarks. The use of the "fan" allows for more consistency in creating the outlines on different images.

In step 510, the user-identified outline points are converted into data coordinates by the digitizing software. TABLE 1 represents the landmarks and outline points of FIG. 7 as stored in an output file. The output file lists the coordinate data in a tabular format, with the x-coordinate listed first followed by the y-coordinate. As indicated in TABLE 1, the two landmark coordinates are listed first, followed by the 40 point coordinates.

TABLE 1

| LM = 2 | |
|---|---|
| 401.00000 | 304.00000 |
| 180.00000 | 347.00000 |
| CURVES = 1 | |
| POINTS = 40 | |
| 401.00000 | 302.00000 |
| 399.00000 | 322.00000 |
| 393.00000 | 337.00000 |
| 386.00000 | 353.00000 |
| 375.00000 | 365.00000 |
| 365.00000 | 376.00000 |
| 356.00000 | 386.00000 |
| 345.00000 | 395.00000 |
| 334.00000 | 400.00000 |
| 320.00000 | 402.00000 |
| 307.00000 | 402.00000 |
| 294.00000 | 401.00000 |

TABLE 1-continued

| | |
|---|---|
| 283.00000 | 400.00000 |
| 271.00000 | 397.00000 |
| 260.00000 | 396.00000 |
| 247.00000 | 391.00000 |
| 236.00000 | 387.00000 |
| 220.00000 | 381.00000 |
| 209.00000 | 373.00000 |
| 194.00000 | 364.00000 |
| 182.00000 | 349.00000 |
| 178.00000 | 330.00000 |
| 183.00000 | 313.00000 |
| 189.00000 | 297.00000 |
| 198.00000 | 283.00000 |
| 207.00000 | 270.00000 |
| 221.00000 | 261.00000 |
| 236.00000 | 254.00000 |
| 248.00000 | 248.00000 |
| 260.00000 | 243.00000 |
| 272.00000 | 240.00000 |
| 287.00000 | 236.00000 |
| 301.00000 | 236.00000 |
| 315.00000 | 235.00000 |
| 331.00000 | 238.00000 |
| 346.00000 | 244.00000 |
| 359.00000 | 252.00000 |
| 371.00000 | 264.00000 |
| 382.00000 | 275.00000 |
| 391.00000 | 288.00000 |

IMAGE = Image1.bmp
ID = 1
SCALE = 0.140234

In order to ensure the coordinate data is aligned properly with the two specified landmarks, the user may employ a software program that utilizes general algorithms to adjust the coordinate data by rotating and translating each data point so that the OFD axis lies along the horizontal axis and that the first point lies at the origin, (x,y)=(0,0). These adjustments do not change the shape of the outline being investigated. The software program may employ the following general algorithm:

Point 1 = Origin: Denote as $X_1, Y_1$
Point 2 = Other end of OFD axis: Denote as $X_2, Y_2$
Determine Slope of Line: $(Y_2 - Y_1)/(X_2 - X_1)$
Determine the angle of the slope: Theta = arctangent(Slope)
For each point in the shape rotate the point clockwise:
    Subtract out the origin such that NewX = X - $X_1$, NewY = Y - $Y_1$
    FinalX = NewX*cos(Theta) + NewY*sin(Theta)
    FinalY = newY*cos(theta) - NewX*sin(theta)

The set of FinalX, FinalY values represent the rotated data points such that the OFD axis lies horizontally. In different scenarios, it may be appropriate to rotate the image in a counter clockwise manner; if this is the case then the formulas for FinalX and FinalY are:

FinalX = NewX*cos(Theta) - NewY*sin(Theta)
FinalY = NewX*sin(Theta) + NewY*cos(Theta)

In step 520, the user may employ software such as the NTSYSPC program (Exeter Software), which uses an elliptical Fourier analysis program to generate a series of best fit curves to the coordinate data using harmonics. The zero harmonic consists of only 2 coefficients and represents only translation (i.e. movement in the x and y direction) and not shape itself so these 2 coefficients are usually not analyzed. Each harmonic comprises four coefficients of interpolation functions that describe the user-identified outline shape. In general, the more harmonics used, the better the fit to the coordinates; however, if too many harmonics are used the fit may be too good since small differences might appear due to poor placement of the outline point during step 500. In this embodiment, the user evaluates the first harmonic (i.e., the four coefficients a1, b1, c1 and d1).

The user may choose alternatives to the method described above for aligning the coordinate data. For example, the user could rotate the image so that the long axis of the shape described by the first harmonic is parallel to the x-axis, or the user can align the image such that the first point of the outline is set equal to the end point of the first harmonic to the x-axis, or the user could combine both of these methods. These options are available as part of the Elliptical Fourier Analysis module in the NTSYSPC program.

In step 530, the determined coefficients may be utilized as markers to assess fetal abnormality by conducting a statistical analysis to compare the patient's determined coefficients with reference parameters derived from reference data of coefficient markers (e.g., a statistical distribution of determined coefficients in the unaffected population and/or affected population). One exemplary method of doing this is to calculate the Mahalanobis Squared Distance (MSD) value for the patient's coefficients.

Prior to determining the outline coefficients, the coordinates may be adjusted by scaling the coordinates so that the area enclosed inside the outline equals 1. The original areas of the enclosed outline could be included as a separate variable in addition to the coefficients as part of the statistical comparison analysis. Also, many shapes change with growth in the fetus. As a result, it may be necessary to adjust the observed coefficients to account for gestational age of the fetus as part of the statistical analysis.

Several other shape analysis methods besides elliptical Fourier analysis may be utilized by the present invention. All of the following methods determine coefficients of functions that may be used as markers to assess fetal abnormality. Some examples of outline methods are:

A. polynomials
B. cubic splines
C. parametric polynomials
D. parametric cubic splines
E. bezier curves
F. Fourier analysis of equally spaced radii
G. dual axis Fourier analysis All of these methods deal with outlines, of which there are four classes—simple open outlines, simple closed outlines, complex open outlines, complex closed outlines. A simple open outline is an open outline that has only one value of y for each x. A complex open outline is an outline that can have more than one y value for each x. Simple closed outlines are closed outlines such that if one draws a line from the center through the outline it only crosses the outline once whereas in a complex outline the line would cross the outline more than once. In most cases an open outline can be analyzed as if it is a closed outline by assuming there is a straight line from the last to first point of the outline or by mirroring all of the coordinates around the x (or y) axis, however the outline can be analyzed as an open outline. Some of the methods above, such as the polynomial method, work with open outlines while others like the elliptical Fourier analysis work with closed outlines. It is also possible to analyze 3-dimensional outlines (x,y,z) in accordance with an alternative embodiment of the present invention.

To provide the reference data to which the determined coefficients are compared in step 530, a statistical algorithm may be utilized to determine the statistical distribution of the coefficients in the unaffected population using a set of coefficients for a series of unaffected pregnancies. The distribution may be defined by a series of reference parameters for each coefficient or pair of coefficients such as means, standard deviations and correlations. The coefficients associated with an outline in a particular patient could be compared to these reference parameters and the chance that the coefficients could be equal to or more extreme than their observed values could be determined.

If affected cases are available then they may be included in the reference data set to determine the statistical distribution of the coefficients in the affected population using a set of coefficients from a series of affected pregnancies. The patient's coefficients could then be compared to the distribution of coefficients in the affected population. Alternatively, the patient's coefficients could be compared to both the unaffected distribution and the affected distribution as defined by the reference parameters. For example, if both the unaffected cases and affected cases are multivariately normally distributed, the distribution function for the multivariate normal distribution can be used with the reference parameters for the unaffected distribution to determine a relative frequency for the unaffected distribution and then again for the affected distribution to determine a relative frequency for the affected distribution, and then a likelihood ratio may be determined. A likelihood ratio equals the quotient of the relative frequency in the affected distribution to the relative frequency in the unaffected distribution. A risk result (e.g., 1 in 100) gives the chance that a patient with the same parameters could have a child with a fetal abnormality. A likelihood ratio gives the relative risk that the patient could have a child with a fetal abnormality.

The likelihood ratio can be used to multiply a prior risk to determine a posterior risk (after accounting for the minor adjustment between odds and risk, if necessary). For example, the prior risk of Down syndrome is often based on maternal age. If the statistical distribution of the determined coefficients are independent of the distribution of other markers, the likelihood ratio could also be used to adjust the risk of Down syndrome determined by the other markers to determine the overall risk of Down syndrome based on the outline and the other markers. Alternatively, if the coefficients are not independent of the other markers, then risk of Down syndrome could be determined by utilizing reference parameters for a combination of the coefficients and the other markers together using multivariate normal distributions or other distribution functions.

Examples of other markers include nuchal translucency, free Beta hCG and PAPP-A, Ductus Venosus, absent or hypoplastic nasal bone observed on ultrasound, maternal blood alpha-fetoprotein, maternal blood hCG, maternal blood unconjugated estriol, maternal blood dimeric inhibin A, maternal urine total estriol, maternal urine beta core fragment, maternal urine hyperglycosylated hCG, maternal blood hyperglycosylated hCG, ultrasound "soft markers" which include for example, nuchal edema or increased nuchal fold, short femur, hyperechogenic bowel, and echogenic foci in the heart, etc.

As mentioned above, the other markers can be combined statistically with the results from the shape analysis to provide a final result to the patient. Alternatively, the medical tests for the other markers could be performed prior to the ultrasound exam and then, when the ultrasound exam is completed, the results of the other marker tests can be thereafter combined with the results from the shape analysis.

For providing reference data according to this embodiment of the present invention, columns 2-5 of TABLE 2A show the results of evaluating the first harmonic (i.e., the four coefficients $a_1$, $b_1$, $c_1$ and $d_1$) of fetal head outlines in a study of 35 unaffected pregnancies in the first trimester. TABLE 2B lists the reference parameters consisting of the mean and standard deviation of each coefficient and the variance/covariance matrix consisting of the variance (standard deviation squared) and covariance between each pair of coefficients and the formula for calculating a Mahalanobis-Squared Distance (MSD) for each case.

TABLE 2A

| ID | a1 | b1 | c1 | d1 |
|---|---|---|---|---|
| 1 | .618923 | −.021438 | .017238 | .512385 |
| 2 | .618007 | −.00636 | .004269 | .513899 |
| 3 | .611512 | −.009105 | .013914 | .519218 |
| 4 | .620708 | .001494 | .005816 | .511672 |
| 5 | .620591 | −.001878 | .002653 | .511512 |
| 6 | .610873 | −.005378 | .009693 | .520104 |
| 7 | .626065 | .002194 | .00969 | .506797 |
| 8 | .610239 | −.022687 | .015904 | .520122 |
| 9 | .619487 | −.009327 | .000085 | .512371 |
| 10 | .61309 | .002649 | .013512 | .518273 |
| 11 | .610239 | .009847 | −.00302 | .520935 |
| 12 | .633193 | −.0167 | .021139 | .500202 |
| 13 | .617141 | −.031007 | .009402 | .513915 |
| 14 | .613927 | −.003108 | .020587 | .517351 |
| 15 | .624268 | .010912 | .002663 | .508347 |
| 16 | .620115 | −.027663 | .02827 | .510862 |
| 17 | .613857 | −.034757 | .023583 | .516377 |
| 18 | .636496 | −.010523 | .021077 | .497571 |
| 19 | .607668 | −.026101 | .003049 | .522709 |
| 20 | .614509 | .004114 | .020143 | .517041 |
| 21 | .627318 | −.034898 | .014111 | .50485 |
| 22 | .605777 | −.018182 | .013938 | .524513 |
| 23 | .606093 | .009761 | .007094 | .524719 |
| 24 | .633498 | −.005676 | .029437 | .500312 |
| 25 | .634393 | −.00556 | .013881 | .499904 |
| 26 | .606259 | .006939 | −.016111 | .52415 |
| 27 | .63582 | −.031021 | .035875 | .497006 |
| 28 | .607238 | −.040385 | .006671 | .522681 |
| 29 | .612626 | −.023636 | −.006856 | .518649 |
| 30 | .6171 | .026204 | −.001128 | .514461 |
| 31 | .640095 | −.022288 | .018631 | .494486 |
| 32 | .625569 | −.012373 | .038643 | .506998 |
| 33 | .611093 | −.02788 | .032891 | .518468 |
| 34 | .629932 | −.03224 | .033393 | .501638 |
| 35 | .608294 | .041921 | −.008744 | .522055 |

TABLE 2B

| Variable | Mean | Std. Dev. |
|---|---|---|
| a1 | −.6189147 | .0099677 |
| b1 | .0104039 | .0183979 |
| c1 | −.0128969 | .0130582 |
| d1 | −.5127587 | .00881 |

| Variance/Covariance Matrix (M) | | | |
|---|---|---|---|
| | a1 | b1 | c1 | d1 |
| a1 | .000099 | −.000035 | .000064 | −.000088 |
| b1 | −.000035 | .000338 | −.000125 | .000036 |
| c1 | .000064 | −.000125 | .00071 | −.00006 |
| d1 | −.000088 | .000036 | −.00006 | .000078 |

$$\mathrm{MSD} = (X - \mu)^T M^{-1} (X - \mu)$$

where:

(X-μ) is a 4 element vector consisting of the patient's 4 coefficients (a1, b1, c1, d1 minus their respective reference means).

$(X-\mu)^T$ is the transpose of the (X-μ) vector $M^{-1}$ is the Inverse of the 4×4 Variance/Covariance Matrix TABLE 2C shows the MSD calculation in the 35 unaffected cases. A cut-off beyond 95% of the observed data was established representing a point halfway between the last 2 MSD values (11.714). TABLE 2D shows the results of 2 patients who happened to be carrying a fetus with Down syndrome, both of which based on their MSD calculation are outliers. As more data from Down syndrome pregnancies are gathered, additional reference parameters (e.g., means, standard deviations, and covariances) based on the Down syndrome cases could be calculated along with other statistical techniques such as likelihood ratios to determine the odds that a patient is carrying a fetus with Down syndrome.

TABLE 2C

| ID | MSD |
|---|---|
| 1 | .5453869 |
| 2 | .72770054 |
| 3 | .86797516 |
| 4 | .99110505 |
| 5 | 1.0513294 |
| 6 | 1.1757276 |
| 7 | 1.3182192 |
| 8 | 1.639374 |
| 9 | 1.7719449 |
| 10 | 1.9632445 |
| 11 | 2.0438778 |
| 12 | 2.0904377 |
| 13 | 2.4440608 |
| 14 | 2.5725717 |
| 15 | 2.6427427 |
| 16 | 2.8276119 |
| 17 | 3.255354 |
| 18 | 3.5018765 |
| 19 | 3.6411678 |
| 20 | 3.7887796 |
| 21 | 3.9182202 |
| 22 | 4.0570078 |
| 23 | 4.5657224 |
| 24 | 4.6067905 |
| 25 | 4.9834947 |
| 26 | 5.5061446 |
| 27 | 5.5437792 |
| 28 | 5.877155 |
| 29 | 6.0931487 |
| 30 | 6.2047977 |
| 31 | 6.3209851 |
| 32 | 6.5548075 |
| 33 | 7.4795723 |
| 34 | 9.0892238 |
| 35 | 14.338667 |

TABLE 2D

| Outcome | a1 | b1 | c1 | d1 | MSD |
|---|---|---|---|---|---|
| 36 | .570043 | −.015975 | .01023 | .558191 | 94.220565 |
| 37 | .58333 | .076813 | −.056937 | .538497 | 403.86348 |

In this embodiment of the present invention, only the data associated with TABLE 2B would have to be stored in the computing device for the statistical comparison analysis of a particular patient to be conducted. This would preserve storage resources in the event of reference data based on very large populations.

Analysis of Fetal Brow Embodiment

Figure 8:
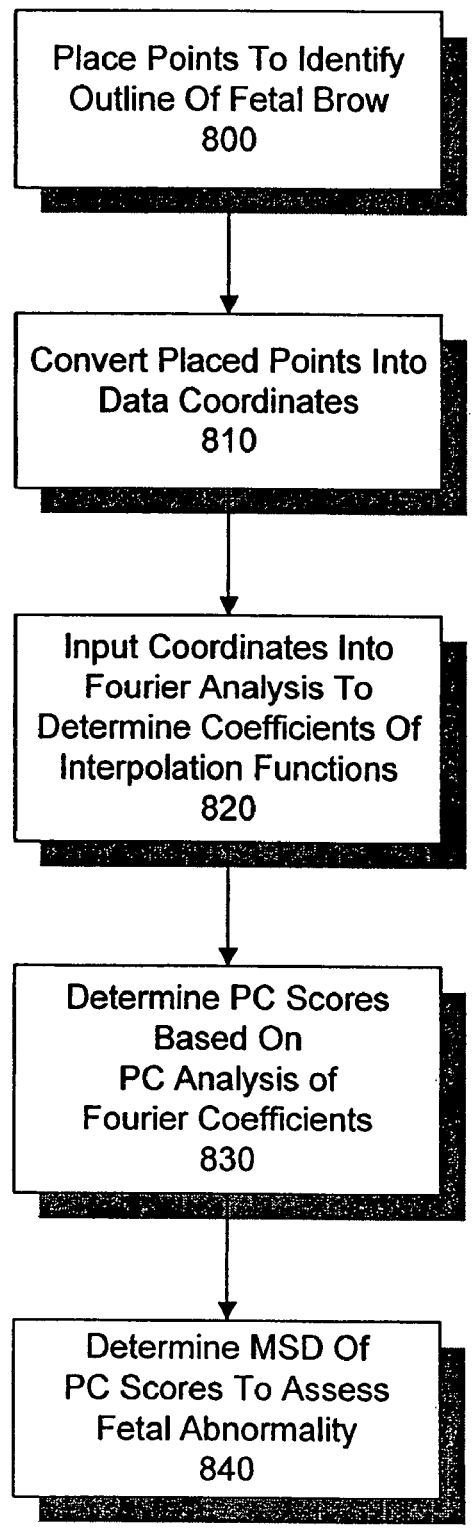
FIG. 8 is a flow chart that depicts a process for utilizing shape analysis of a fetal brow to determine risk of fetal abnormality in accordance with an embodiment of the present invention.

FIG. 8 provides an example embodiment of the present invention in which the shape of a fetal brow is analyzed using 3-D ultrasound to assess fetal abnormality. In traditional 2-D ultrasound the challenge to the sonographer is obtaining an image that is in the proper plane of view. The ability to consistently obtain the same angle and depth of view of the fetus requires subjective decision making during the ultrasound exam. Thus it is difficult to obtain consistent views of each fetus from exam to exam. This increases error when trying to analyze shapes from these images.

Figure 9:
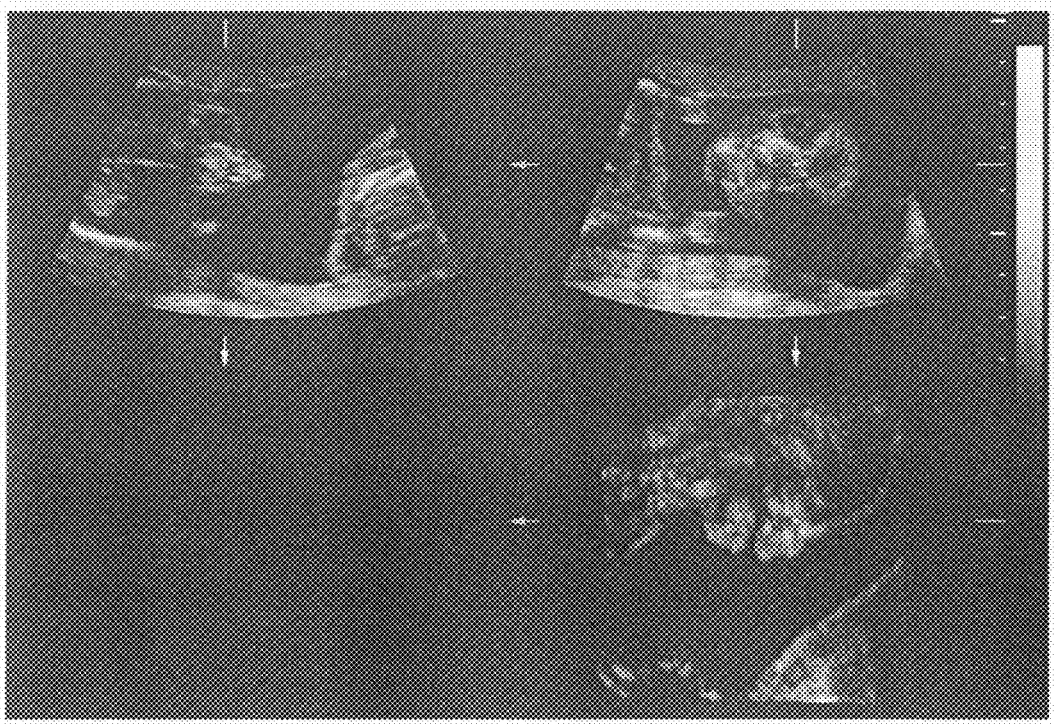
FIG. 9 is a screen shot that depicts outlining of a fetal brow in accordance with an embodiment of the present invention.

3D ultrasound allows for the simultaneous visualization of the fetus in 3 separate 2-D planes, as shown in FIG. 9. These three planes are called the sagittal (side-view), coronal (front-view) and transverse (top-view). In FIG. 9, the top left image represents the transverse plane, the top right represents the coronal plane, and the bottom right represents the sagittal plane.

Misalignment of an image in any given plane distorts the images in the other two planes. Therefore, in order to perform proper 2-D image analysis of any given plane, the image should first be aligned properly in all three planes. For example, to analyze an image in the sagittal plane, a user can assure a proper view by aligning the fetus in the coronal and transverse views. In addition, by choosing a landmark in each plane (e.g. the white dot placed at the bridge of the nose in the FIG. 9) the depth of the section can also be defined. Using landmarks and aligning the fetus in all three planes can insure that the view of each fetus in any given plane is the same and thus reduce variation in shape due to differences in ultrasound technique. Ultimately this will improve the ability to see changes due to biological effects. 3D ultrasound further allows for image manipulation after the completion of the examination. Therefore, after capturing a 3-D image the operator can later rotate that image to the appropriate view.

The use of 3D sonography is a recent advance in prenatal ultrasound. The technique generates a multiplanar display of separate images in the coronal, sagittal and transverse planes obtained by the ascertainment of a single "volume". Once the volume is obtained the images in each plane may be rotated to provide consistent and reproducible planes as part of a "post processing" evaluation. This advance was previously unobtainable using conventional 2D sonographic techniques. Once a given desired image and plane is obtained, it may be superimposed on a digitized screen where geometric morphometric analysis may be performed.

According to this embodiment, a fetal brow is analyzed in the sagittal plane—from the bridge of the nose to the midportion of the top of the skull. The fetal image of FIG. 9 is obtained by 3-D ultrasound (e.g., UCD 300a), saved as a bit-map image and transferred to another computer (e.g., UCD 300b). The sonographer (e.g., user 400a) places the landmark at the bridge of the nose in each plane.

Figure 10:
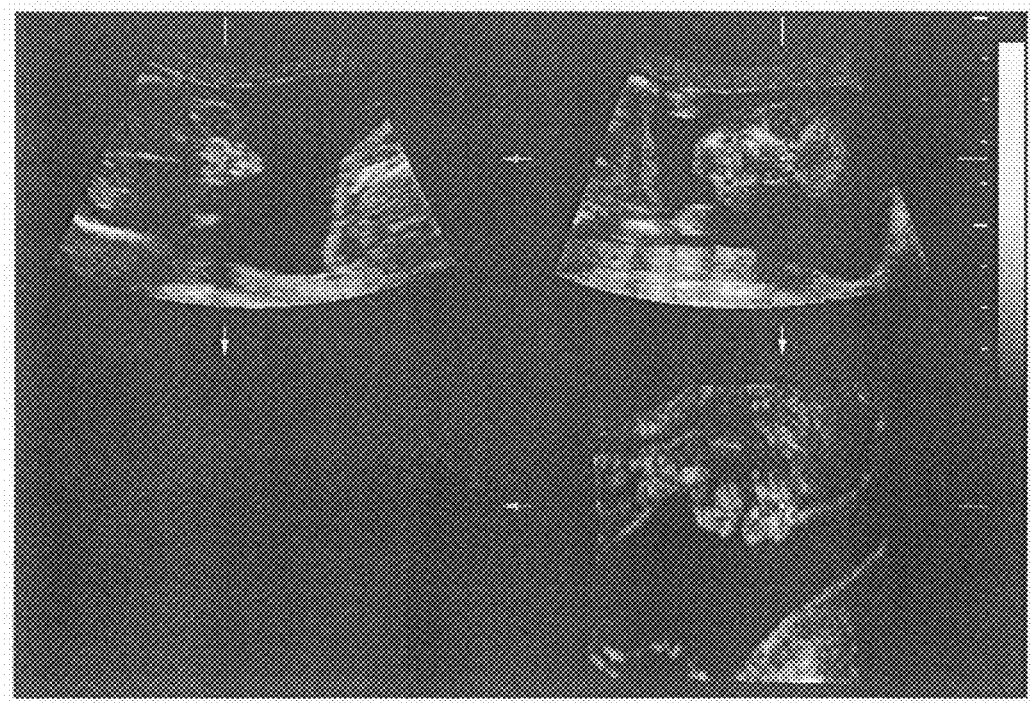
FIG. 10 is a screen shot that depicts outlining of a fetal brow in accordance with an embodiment of the present invention.

In step 800, a user (e.g., user 400b) employs digitizing software to create an outline of the fetal brow to be analyzed. As illustrated in FIG. 10, the user first places two landmark points on the fetal head in the sagittal plane—one at the bridge of the nose and the other at the midportion of the top of the skull. Once these landmarks are correctly in place, the user employs a software program that utilizes a general algorithm to find a point that has the same horizontal component as the landmark on the bridge of the nose, and the same vertical component as the landmark at the top of the head. Once this point is found, a series of 16 lines of equal length are drawn, as shown in FIG. 11.

Figure 11:
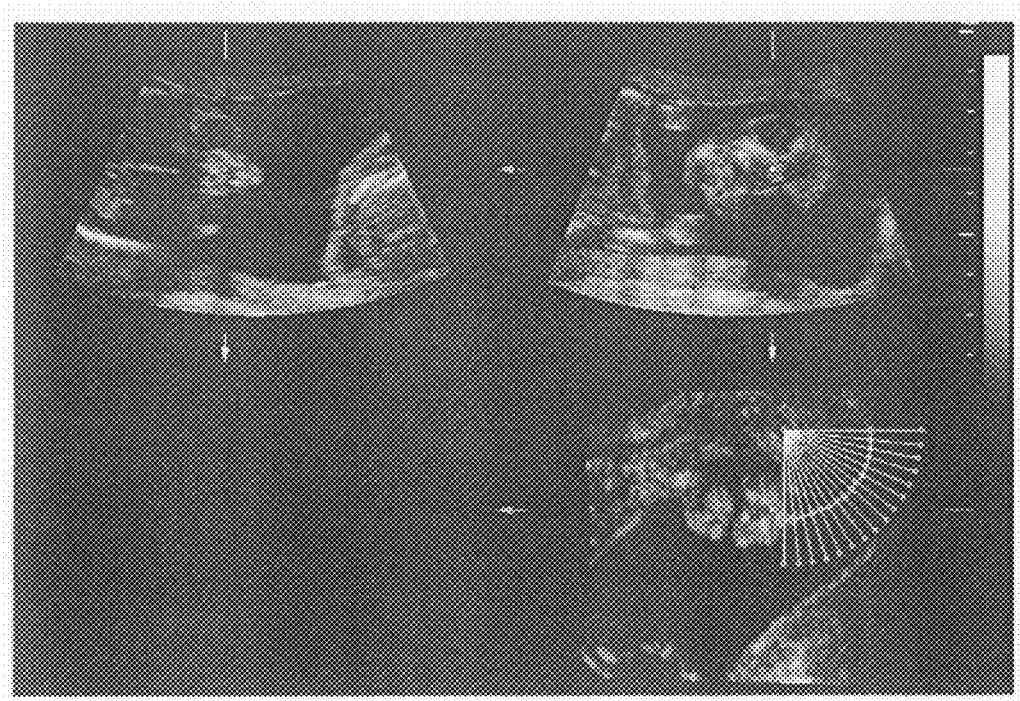
FIG. 11 is a screen shot that depicts outlining of a fetal brow in accordance with an embodiment of the present invention.
Figure 12:
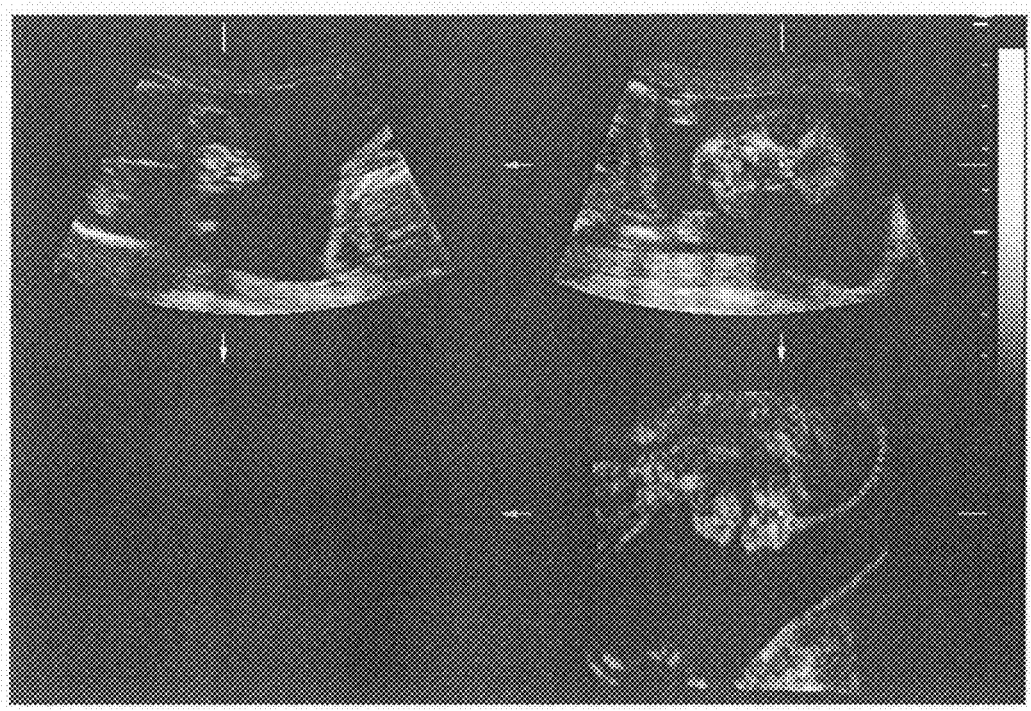
FIG. 12 is a screen shot that depicts outlining of a fetal brow in accordance with an embodiment of the present invention.

The first line in FIG. 11 starts from the center point and goes through the landmark at the bridge of the nose. The remaining lines start at the center point and then are rotated at 6 degrees from the previous line in a counterclockwise manner until a line is drawn through the point at the top of the head which is at a 90 degree angle from the initial line. Once this "fan" is drawn, the user may place points on the outline of the skull where it crossed the equidistant lines of the "fan" using the digitizing software. This method ensures the user to get curves with less human error and more reproducibility. FIG. 12 shows the 16 resulting points placed in the sagittal plane.

In step 810, the user-identified outline points are converted into data coordinates by the digitizing software. The user may choose to use only the first eight points in subsequent analysis since these points more determinatively represent the fetal brow.

In step 820, an elliptical Fourier analysis is employed using three harmonics (i.e., three sets of coefficients). The determined coefficients are utilized as markers to assess fetal abnormality by conducting a statistical analysis, such as a principal component (PC) analysis.

In step 830, PC scores are determined based on a PC analysis of the determined Fourier coefficients, and in step 840, the MSD values of the PC scores are calculated. As discussed above, this shape analysis may also be combined with other markers to more completely assess fetal abnormality.

The PC analysis utilized by this embodiment is a statistical technique used with multivariate data to reduce the number of variables used in further statistical analysis. (It can also be used as an exploratory analysis to see which of the variables are most important). The PC analysis is a standard statistical technique that generates a set of linear combinations of the underlying variables. These linear combinations represent new variables that can be used in other statistical analyses. The first linear combination is the most important variable and so on. Higher numbered principal components can be dropped from further analyses since they tend to represent noise. Once the principle components are determined (e.g., $0.3X_1 + 0.2X_2 + 0.4X_3 \ldots$), the PC scores can then be calculated which can be used as the variables in an MSD calculation.

For providing reference data according to this embodiment of the present invention, TABLE 4 shows the results of evaluating the first three harmonics (i.e., three sets of the four coefficients A, B, C and D) of fetal brow outlines in a study of 32 normal pregnancies.

TABLE 4

| image | outcome | addnl_img | a1 | b1 | c1 | d1 | a2 | b2 | c2 | d2 | a3 | b3 | c3 | d3 |
|---|---|---|---|---|---|---|---|---|---|---|---|---|---|---|
| 1-4x2 | 0 | 0 | −1.53 | −.0426 | −.00609 | −.205 | .000102 | .00658 | .0751 | −.00803 | −.163 | −.0141 | .00464 | −.0148 |
| 865-16x2 | 0 | 0 | −1.52 | −.0427 | .000763 | −.204 | −.000096 | .00607 | .071 | .000297 | −.162 | −.014 | −.000216 | −.0166 |
| 1-7x | 0 | 0 | −1.5 | −.0434 | .000701 | −.208 | .00116 | .00865 | .0756 | −.00421 | −.161 | −.0123 | .0103 | −.0123 |
| 1-27x2 | 0 | 0 | −1.5 | −.0478 | −.00868 | −.209 | .000064 | .00832 | .0771 | −.0112 | −.161 | −.0163 | .00577 | −.0116 |
| 1-5x2 | 0 | 0 | −1.36 | −.059 | −.00291 | −.233 | −.000516 | .0105 | .0887 | −.00506 | −.14 | −.0194 | .00354 | −.0119 |
| 1-9x | 0 | 0 | −1.38 | −.0487 | .0112 | −.225 | −.000699 | .00801 | .0785 | .00928 | −.145 | −.0153 | −.0000916 | −.0167 |
| 865-1x2 | 0 | 0 | −1.57 | −.0347 | .0212 | −.202 | .00101 | .00913 | .0805 | .0202 | −.168 | −.00939 | −.00341 | −.00737 |
| 1-2x | 0 | 0 | −1.48 | −.0377 | .0133 | −.215 | .000543 | .00961 | .085 | .0106 | −.158 | −.0104 | .00267 | −.00535 |
| 2-20x2 | 0 | 0 | −1.67 | −.0407 | −.0159 | −.187 | −.0000525 | .00626 | .0685 | −.0166 | −.18 | −.0141 | .00452 | −.014 |
| 865-10x2 | 0 | 0 | −1.27 | −.0647 | .00922 | −.246 | −.00123 | .0109 | .0872 | .0062 | −.13 | −.02 | .00275 | −.0167 |
| 865-15x2 | 0 | 0 | −1.45 | −.0362 | .0204 | −.218 | −.00224 | .00905 | .082 | .0209 | −.153 | −.0119 | −.00631 | −.0124 |
| 1-12x1 | 0 | 0 | −1.64 | −.0383 | −.00745 | −.187 | .000816 | .00495 | .0604 | −.0124 | −.177 | −.0124 | .0108 | −.0201 |
| 1-29x2 | 0 | 0 | −1.44 | −.0539 | −.00597 | −.216 | .00316 | .00857 | .0763 | −.0134 | −.152 | −.0145 | .0165 | −.0186 |
| 865-18x2 | 0 | 0 | −1.81 | −.0216 | .00424 | −.173 | −.000255 | .0042 | .065 | .00434 | −.198 | −.00702 | −.00122 | −.00975 |
| 865-12x2 | 0 | 0 | −1.54 | −.0313 | .015 | −.205 | −.00311 | .00838 | .0791 | .0182 | −.165 | −.0119 | −.0111 | −.01 |
| 1-6x2 | 0 | 0 | −1.5 | −.0455 | −.00627 | −.21 | −.0002 | .00953 | .0831 | −.00785 | −.162 | −.0151 | .00415 | −.00405 |
| 865-6x2 | 0 | 0 | −1.66 | −.0336 | −.0104 | −.191 | −.000402 | .00666 | .0773 | −.0113 | −.18 | −.0119 | .0032 | −.00458 |
| 865-11x2 | 0 | 0 | −1.39 | −.0673 | −.0116 | −.224 | .00189 | .0084 | .0754 | −.0158 | −.143 | −.0205 | .00992 | −.0251 |
| 865-7x2 | 0 | 0 | −1.36 | −.0427 | .0272 | −.234 | −.00137 | .0128 | .092 | .0263 | −.143 | −.0123 | −.00534 | −.00475 |
| 865-9x2 | 0 | 0 | −1.87 | −.0212 | .00799 | −.165 | −.0012 | .00491 | .0558 | .00881 | −.204 | −.00773 | −.0034 | −.0178 |
| 1-30x2 | 0 | 0 | −1.31 | −.0799 | −.0141 | −.239 | .0021 | .0138 | .0851 | −.0225 | −.134 | −.0235 | .0205 | −.0197 |
| 1-13x1 | 0 | 0 | −1.3 | −.0583 | .014 | −.24 | −.00241 | .00913 | .0805 | .0123 | −.131 | −.0191 | −.00154 | −.025 |
| 865-3xx2 | 0 | 0 | −1.99 | −.0176 | .0217 | −.156 | −.00203 | .00869 | .0563 | .0251 | −.221 | −.00685 | −.0134 | −.00767 |
| 865-8x2 | 0 | 0 | −1.9 | −.0272 | −.0168 | −.164 | .00109 | .0053 | .0601 | −.0231 | −.209 | −.00858 | .0175 | −.00902 |
| 865-14x2 | 0 | 0 | −2.16 | −.026 | −.0209 | −.142 | .000559 | .00425 | .0464 | −.0211 | −.238 | −.00879 | .00466 | −.0176 |
| 2-18x2 | 0 | 0 | −1.98 | −.0161 | .0138 | −.154 | −.000513 | .00284 | .0467 | .0112 | −.215 | −.00484 | .00322 | −.0243 |
| 1-28x2 | 0 | 0 | −1.39 | −.0642 | −.00215 | −.22 | .000798 | .00732 | .0643 | −.00749 | −.144 | −.02 | .0106 | −.035 |
| 2-19x2 | 0 | 0 | −1.4 | −.0598 | .00756 | −.232 | .00114 | .016 | .101 | .00485 | −.145 | −.0183 | .0018 | .00274 |
| 1-1x | 0 | 0 | −1.14 | −.0995 | .0115 | −.272 | −.000611 | .0122 | .0868 | .0042 | −.108 | −.0301 | .00714 | −.0274 |
| 1-11x2 | 0 | 0 | −1.19 | −.111 | −.0167 | −.266 | .000575 | .0157 | .0974 | −.024 | −.116 | −.0352 | .0161 | −.0141 |
| 1-14x | 0 | 0 | −1.62 | −.028 | .0307 | −.201 | −.00573 | .014 | .0889 | .0371 | −.174 | −.0128 | −.0219 | .00249 |
| 1-10x2 | 0 | 0 | −1.18 | −.0676 | .0359 | −.271 | −.00495 | .0222 | .102 | .0335 | −.12 | −.0211 | −.00789 | −.00529 |

TABLE 5 shows the resulting PC analysis of the Fourier coefficients.

TABLE 5

PRINCIPAL COMPONENT ANALYSIS
. pca a1-d3 if outcome == 0 & addnl__img == 0, mineigen(1.0) (obs = 32)

(principal components; 3 components retained)

| Component | Eigenvalue | Difference | Proportion | Cumulative |
|---|---|---|---|---|
| 1 | 5.96194 | 1.82595 | 0.4968 | 0.4968 |
| 2 | 4.13599 | 3.09719 | 0.3447 | 0.8415 |
| 3 | 1.03880 | 0.57715 | 0.0866 | 0.9281 |
| 4 | 0.46165 | 0.21530 | 0.0385 | 0.9665 |
| 5 | 0.24635 | 0.14543 | 0.0205 | 0.9871 |
| 6 | 0.10092 | 0.06229 | 0.0084 | 0.9955 |
| 7 | 0.03863 | 0.02910 | 0.0032 | 0.9987 |
| 8 | 0.00953 | 0.00396 | 0.0008 | 0.9995 |
| 9 | 0.00558 | 0.00520 | 0.0005 | 0.9999 |
| 10 | 0.00038 | 0.00022 | 0.0000 | 1.0000 |
| 11 | 0.00016 | 0.00010 | 0.0000 | 1.0000 |
| 12 | 0.00006 | | 0.0000 | 1.0000 |

Scoring Coefficients

| Variable | 1 | 2 | 3 |
|---|---|---|---|
| a1 | 0.39500 | −0.01100 | −0.08986 |
| b1 | −0.36639 | 0.18716 | 0.08292 |
| c1 | 0.06718 | 0.44499 | −0.25403 |
| d1 | −0.40589 | −0.01047 | 0.07023 |
| a2 | −0.03619 | −0.41808 | 0.20309 |
| b2 | 0.33650 | 0.17614 | 0.25352 |
| c2 | 0.36181 | 0.14020 | 0.32808 |
| d2 | 0.02593 | 0.46832 | −0.22168 |
| a3 | 0.39740 | −0.02115 | −0.11651 |
| b3 | −0.36383 | 0.15894 | 0.08324 |
| c3 | 0.06250 | −0.46168 | 0.10331 |
| d3 | −0.01183 | 0.28823 | 0.78874 |

TABLE 5-continued

PRINCIPAL COMPONENT ANALYSIS
. pca a1-d3 if outcome == 0 & addnl__img == 0, mineigen(1.0) (obs = 32)

| Variable | Mean | Std. Dev. |
|---|---|---|
| a1 | −1.53125 | .2485798 |
| b1 | −.04715 | .0221123 |
| c1 | .0037642 | .0151056 |
| d1 | −.2098125 | .0330263 |
| a2 | −.000394 | .0018714 |
| b2 | .0091534 | .0040555 |
| c2 | .0765344 | .014202 |
| d2 | .0015418 | .0170104 |
| a3 | −.1625 | .0312441 |
| b3 | −.0149906 | .0066018 |
| c3 | .0026395 | .0092017 |
| d3 | −.0135719 | .0085003 |

In this embodiment, the first 3 principal components are retained and used to calculate the associated PC variables. First a z-score for each coefficient is calculated by subtracting the mean of the coefficient and then dividing the difference by the standard deviation of the coefficient from TABLE 5. Each PC variable is then created by multiplying the scoring coefficient for each (a1-d3) by the z-score for each variable and then summing the 12 products, as shown in TABLE 6.

TABLE 6

| image | outcome | addnl__img | PCA1 | PCA2 | PCA3 |
|---|---|---|---|---|---|
| 1-4x2 | 0 | 0 | −.4907767 | −.8738552 | .0987127 |
| 865-16x2 | 0 | 0 | −.6085553 | −.2783825 | −.4990045 |
| 1-7x | 0 | 0 | −.2317154 | −.874534 | .4810387 |
| 1-27x2 | 0 | 0 | .0218282 | −.9802006 | .569997 |
| 1-5x2 | 0 | 0 | 1.670697 | −.3829324 | .4203361 |
| 1-9x | 0 | 0 | .6840906 | .4666384 | −.7679284 |
| 865-1x2 | 0 | 0 | −.6142922 | 1.508776 | .3821437 |
| 1-2x | 0 | 0 | .0732714 | .8884591 | .8576227 |
| 2-20x2 | 0 | 0 | −1.432505 | −1.382093 | .4184196 |
| 865-10x2 | 0 | 0 | 2.309402 | .2540324 | −.5981961 |
| 865-15x2 | 0 | 0 | .2062483 | 2.133314 | −.6064944 |
| 1-12x1 | 0 | 0 | −1.716844 | −1.812474 | −.44028 |
| 1-29x2 | 0 | 0 | .3513637 | −2.44019 | .2868603 |
| 865-18x2 | 0 | 0 | −2.942221 | .4870823 | .2135515 |
| 865-12x2 | 0 | 0 | −.5070165 | 2.407711 | −.391572 |
| 1-6x2 | 0 | 0 | .1698279 | −.2595708 | 1.379145 |
| 865-6x2 | 0 | 0 | −1.33174 | −.3922991 | 1.348731 |
| 865-11x2 | 0 | 0 | 1.119487 | −2.558559 | −.6279961 |
| 865-7x2 | 0 | 0 | 1.386343 | 2.689931 | .3561011 |
| 865-9x2 | 0 | 0 | −3.317 | .6986394 | −.8962799 |
| 1-30x2 | 0 | 0 | 2.653671 | −3.064767 | .526195 |
| 1-13x1 | 0 | 0 | 1.737869 | .6931306 | −1.907204 |
| 865-3xx2 | 0 | 0 | −3.596458 | 2.816385 | −.203151 |
| 865-8x2 | 0 | 0 | −3.22584 | −2.18013 | 1.356439 |
| 865-14x2 | 0 | 0 | −4.802877 | −1.925512 | .2700403 |
| 2-18x2 | 0 | 0 | −4.344046 | .1713885 | −1.659267 |
| 1-28x2 | 0 | 0 | .7005095 | −2.296043 | −2.21848 |
| 2-19x2 | 0 | 0 | 2.251043 | .7969418 | 2.307821 |
| 1-1x | 0 | 0 | 4.38609 | −.9528349 | −1.857011 |
| 1-11x2 | 0 | 0 | 5.014206 | −2.781211 | .8650386 |
| 1-14x | 0 | 0 | −.0283105 | 5.296726 | .5011879 |
| 1-10x2 | 0 | 0 | 4.454249 | 4.126434 | .0334842 |

The PC variables are used in an MSD calculation to create an atypicality index, as shown in TABLE 7. The PC variables are independent of each other so the variance/covariance matrix is not needed. A cut-off of MSD>7.81 (95$^{th}$ percentile of the expected $X^2$ with 3 d.o.f.) was used to define outliers.

TABLE 7

| Variable | Obs | Mean | Std. Dev. |
|---|---|---|---|
| PCA1 | 32 | −1.15e−08 | 2.441709 |
| PCA2 | 32 | −2.79e−09 | 2.033714 |
| PCA3 | 32 | 2.44e−09 | 1.019216 |

$MSB = (PCA1/2.441709)\hat{\,}2 + (PCA2/2.033714)\hat{\,}2 + (PCA3/1.019216)\hat{\,}2$ TABLE 8A shows the coefficients from an elliptical Fourier analysis for 6 affected cases and 8 images that represent an additional image from a patient in the reference set. The MSD is calculated using the means and standard deviations of the coefficients, the PC scoring coefficients and the MSD formula for the 32 unaffected patients, the six affected patients and 8 additional images from patients in the group. The results are shown in TABLE 8B. The 3 outliers were all abnormal (Trisomy 21, Trisomy 18, and one fetus with multiple congenital anomalies). Two Trisomy 21 and one case with an unbalanced translocation were not outliers. The affected cases were 1-3× Trisomy 18, 2-21×2 campomelic dysplasia, 2-23×2, 2-23×3, 2-23×4 (same patient) Trisomy 21, 865×2 Trisomy 21, 865-5×2 Trisomy 21, 865-17×2 translocation.

TABLE 8A

| image | outcome | addnl_img | a1 | b1 | c1 | d1 | a2 | b2 | c2 | d2 | a3 | b3 | c3 | d3 |
|---|---|---|---|---|---|---|---|---|---|---|---|---|---|---|
| 865-11xx2 | 0 | 1 | −1.8 | −.0179 | .0173 | −.174 | −.00083 | .00425 | .0647 | .0179 | −.196 | −.00566 | −.00494 | −.0109 |
| 865-13xx2 | 0 | 1 | −1.55 | −.0308 | .0201 | −.202 | −.00266 | .00797 | .0725 | .0213 | −.165 | −.0111 | −.00747 | −.0183 |
| 1-12x2 | 0 | 1 | −1.91 | −.0263 | −.0153 | −.163 | −.000187 | .00376 | .0617 | −.0147 | −.209 | −.00962 | .0013 | −.00838 |
| 1-14x2 | 0 | 1 | −1.25 | −.053 | .0353 | −.25 | −.00137 | .0141 | .0898 | .0317 | −.129 | −.0138 | −.00302 | −.0125 |
| 1-14x3 | 0 | 1 | −1.19 | −.0866 | .0063 | −.26 | −.000359 | .0105 | .0853 | .0000546 | −.116 | −.0263 | .00843 | −.0262 |
| 1-12x3 | 0 | 1 | −1.56 | −.0535 | −.021 | −.204 | .00453 | .0105 | .079 | −.0298 | −.167 | −.0141 | .0235 | −.00989 |
| 2-23x2 | 1 | 0 | −1.43 | −.0371 | .0264 | −.223 | −.00117 | .0118 | .0906 | .0265 | −.152 | −.0107 | −.00682 | −.00278 |
| 865-17x2 | 1 | 0 | −1.34 | −.0532 | .00953 | −.24 | −.00186 | .0136 | .0975 | .00848 | −.138 | −.0172 | −.0011 | −.00345 |
| 865-5x2 | 1 | 0 | −1.5 | −.0568 | −.018 | −.208 | .00261 | .00753 | .0721 | −.024 | −.159 | −.0172 | .0156 | −.0186 |
| 1-3x | 1 | 0 | −1.52 | −.0561 | −.0255 | −.212 | .00157 | .0125 | .0884 | −.0314 | −.163 | −.0181 | .0177 | .000243 |
| 2-21x2 | 1 | 0 | −1.23 | −.0604 | .0336 | −.252 | −.00684 | .013 | .0829 | .0362 | −.125 | −.0213 | −.0167 | −.0232 |
| 865-2x2 | 1 | 0 | −1.3 | −.0456 | .0409 | −.242 | −.0086 | .0146 | .0837 | .0455 | −.133 | −.018 | −.022 | −.0208 |
| 2-23x4 | 1 | 1 | −1.5 | −.04 | .00436 | −.211 | −.00322 | .00833 | .0793 | .00699 | −.158 | −.0156 | −.00813 | −.0131 |
| 2-23x3 | 1 | 1 | −1.58 | −.05 | −.0167 | −.196 | .00368 | .00868 | .0656 | −.0284 | −.17 | −.0133 | .0283 | −.0189 |

TABLE 8B

| image | outcome | addnl_img | MSD |
|---|---|---|---|
| 1-4x2 | 0 | 0 | .2344088 |
| 865-16x2 | 0 | 0 | .3205591 |
| 1-7x | 0 | 0 | .4166765 |
| 1-27x2 | 0 | 0 | .5451415 |
| 1-5x2 | 0 | 0 | .6737114 |
| 1-9x | 0 | 0 | .6988295 |
| 865-1x2 | 0 | 0 | .754262 |
| 1-2x | 0 | 0 | .8997956 |
| 2-20x2 | 0 | 0 | .9745739 |
| 865-10x2 | 0 | 0 | 1.254639 |
| 865-15x2 | 0 | 0 | 1.461579 |
| 1-12x1 | 0 | 0 | 1.475262 |
| 1-29x2 | 0 | 0 | 1.539608 |
| 865-18x2 | 0 | 0 | 1.55325 |
| 865-12x2 | 0 | 0 | 1.592335 |
| 1-6x2 | 0 | 0 | 1.852124 |
| 865-6x2 | 0 | 0 | 2.085814 |
| 865-11x2 | 0 | 0 | 2.172602 |
| 865-7x2 | 0 | 0 | 2.193894 |
| 865-9x2 | 0 | 0 | 2.736778 |
| 1-30x2 | 0 | 0 | 3.718682 |
| 1-13x1 | 0 | 0 | 4.124299 |
| 865-3xx2 | 0 | 0 | 4.127046 |
| 865-8x2 | 0 | 0 | 4.665785 |
| 865-14x2 | 0 | 0 | 4.835767 |
| 2-18x2 | 0 | 0 | 5.822632 |
| 1-28x2 | 0 | 0 | 6.094747 |
| 2-19x2 | 0 | 0 | 6.130581 |
| 1-1x | 0 | 0 | 6.765957 |
| 1-11x2 | 0 | 0 | 6.807669 |
| 1-14x | 0 | 0 | 7.025152 |
| 1-10x2 | 0 | 0 | 7.445808 |
| 865-11xx2 | 0 | 1 | 2.216359 |
| 865-13xx2 | 0 | 1 | 2.848514 |
| 1-12x2 | 0 | 1 | 2.850898 |
| 1-14x2 | 0 | 1 | 2.998304 |
| 1-14x3 | 0 | 1 | 4.574026 |
| 1-12x3 | 0 | 1 | 7.325252 |
| 2-23x2 | 1 | 0 | 2.310336 |
| 865-17x2 | 1 | 0 | 2.346174 |
| 865-5x2 | 1 | 0 | 2.474172 |
| 1-3x | 1 | 0 | 10.08229 |
| 2-21x2 | 1 | 0 | 12.61865 |
| 865-2x2 | 1 | 0 | 15.38419 |
| 2-23x4 | 1 | 1 | .6735099 |
| 2-23x3 | 1 | 1 | 4.372908 |

In this embodiment of the present invention, only the scoring coefficients, means and standard deviations of the coefficients from TABLE 5 and the standard deviations of the PC variables in TABLE 7 would have to be stored in the computing device for the statistical comparison analysis of a particular patient to be conducted. This would preserve storage resources in the event of reference data based on very large populations.

Several embodiments of the invention are specifically illustrated and/or described herein. However, it will be appreciated that modifications and variations of the invention are covered by the above teachings and within the purview of the appended claims without departing from the spirit and intended scope of the invention.

What is claimed is:

1. A computer-implemented method for utilizing shape analysis to assess human fetal abnormality, comprising:
  providing a computer processing system comprising:
    at least one computer processor for processing data;
    a storage medium for storing data;

an interface for receiving coordinates of points identifying an anatomical shape in a human fetal image;
determining a plurality of coefficients, said plurality of coefficients are mathematical function coefficients from one or more mathematical functions that describe the identified anatomic shape; and
utilizing a plurality of the determined coefficients as markers to assess human fetal abnormality.

2. A method of claim 1 wherein said determining step comprises determining a plurality of coefficients of a plurality of different mathematical functions.

3. A method of claim 1 wherein said determining step comprises determining at least four coefficients.

4. A method of claim 1 wherein said determining step comprises determining at least twelve coefficients.

5. A method of claim 1 wherein said determining step comprises determining a plurality of coefficients of at least three different mathematical functions.

6. A method of claim 1 wherein said determining step determines a plurality of coefficients which comprises determining at least one coefficient from a first mathematical function and at least one other coefficient from a second mathematical function.

7. A method of claim 1 wherein said step of utilizing said plurality of coefficients comprises utilizing said plurality of coefficients as markers to assess a chromosomal abnormality.

8. A method of claim 7 wherein said step of utilizing said plurality of coefficients comprises utilizing said plurality of coefficients as markers to assess the chromosomal abnormality Down syndrome.

9. A method of claim 1 wherein said step of utilizing said plurality of coefficients comprises utilizing said plurality of coefficients as markers to assess the fetal abnormality Spina Bifida.

10. A method of claim 1 wherein the plurality of coefficients are determined by a Fourier analysis.

11. A method of claim 1 wherein the plurality of coefficients are determined by a shape analysis method selected from the group consisting of elliptical Fourier analysis, polynomials, cubic splines, parametric polynomials, parametric cubic splines, bezier curves, Fourier analysis of equally spaced radii and dual axis Fourier analysis.

12. A method of claim 1 wherein a plurality of the determined coefficients are utilized as markers to assess human fetal abnormality in the first trimester.

13. A method of claim 1 wherein said step of utilizing a plurality of the determined coefficients as markers comprises conducting a statistical analysis on the determined coefficients.

14. A method of claim 13 wherein said step of conducting a statistical analysis comprises comparing a plurality of the determined coefficients with reference parameters derived from a statistical distribution of determined coefficients in an unaffected population and/or affected population.

15. A method of claim 14 wherein said step of conducting a statistical analysis on the plurality of the determined coefficients comprises conducting at least one of a means calculation, a standard deviation calculation and a correlation calculation.

16. A method of claim 14 wherein said step of conducting a statistical analysis on the plurality of the determined coefficients comprises conducting a principal component analysis.

17. A method of claim 1 wherein said step of utilizing a plurality of the determined coefficients as markers comprises utilizing said markers in combination with one or more additional markers to assess human fetal abnormality.

18. A method of claim 17 wherein said step of utilizing one or more additional markers includes utilizing at least one biochemical marker selected from the group consisting of free Beta hCG, PAPP-A, maternal blood alpha-fetoprotein, maternal blood hCG, maternal blood unconjugated estriol, maternal blood dimeric inhibin A, maternal urine total estriol, maternal urine beta core fragment, maternal urine hyperglycosylated hCG and maternal blood hyperglycosylated hCG.

19. A method of claim 17 wherein said step of utilizing one or more additional markers includes utilizing at least one ultrasound marker selected from the group consisting of nuchal translucency, Ductus Venosus, absent or hypoplastic nasal bone, nuchal edema, short femur, hyperechogenic bowel and echogenic foci in the heart.

20. A method of claim 1 further comprising the step of:
adjusting the received coordinates to align the anatomical shape according to a particular axis before the coefficients are determined.

21. A method of claim 1 further comprising the step of:
adjusting the received coordinates before the coefficients are determined by at least one of translating the coordinates, rotating the coordinates and scaling the coordinates.

22. A method of claim 21 wherein the step of utilizing a plurality of the determined coefficients as markers comprises conducting a statistical analysis on a plurality of the determined coefficients.

23. A method of claim 22 wherein the step of conducting a statistical analysis comprises comparing a plurality of the determined coefficients with reference parameters derived from a statistical distribution of a plurality of the determined coefficients in an unaffected population and/or affected population.

24. A computer-implemented method according to claim 1 further comprising the step of providing an imaging apparatus for generating the human fetal image.

25. An apparatus for utilizing shape analysis to assess human fetal abnormality, comprising:
a processor; and
a memory storing instructions, said instructions adapted to be executed by said processor to:
receive coordinates of points identifying an anatomical shape in a human fetal image;
determine a plurality of coefficients, said plurality of coefficients are mathematical function coefficients from one or more mathematical functions that describe the identified anatomic shape; and
utilize a plurality of the determined coefficients as markers to assess human fetal abnormality.

26. An apparatus according to claim 25 wherein said memory storing instructions adapted to be executed by said processor to determine a plurality of coefficients comprising at least one coefficient from a first mathematical function and at least one coefficient from a second mathematical function.

27. An apparatus according to claim 25 wherein said memory storing instructions adapted to be executed by said processor to determine at least four coefficients.

28. An apparatus according to claim 25 wherein said memory storing instructions adapted to be executed by said processor to determine at least twelve coefficients.

29. An apparatus according to claim 25 wherein said memory storing instructions adapted to be executed by said processor to determine a plurality of coefficients of at least three different mathematical functions.

30. An apparatus according to claim 25 wherein said memory storing instructions adapted to be executed by said processor to determine at least one coefficient from a first mathematical function and at least one other coefficient from a second mathematical function.

31. A system for utilizing shape analysis to assess human fetal abnormality, comprising:
- means for receiving coordinates of points identifying an anatomic shape in a human fetal image;
- means for determining a plurality of coefficients, said plurality of coefficients are mathematical function coefficients from one or more mathematical functions that describe the identified anatomic shape; and
- means for utilizing a plurality of the determined coefficients as markers to assess human fetal abnormality.

32. A system according to claim 31 wherein said determining means comprises means for determining a plurality of coefficients of a plurality of different mathematical functions.

33. A system according to claim 31 wherein said determining means comprises means for determining at least four coefficients.

34. A system according to claim 31 wherein said determining means comprises means for determining at least twelve coefficients.

35. A system according to claim 31 wherein said determining means comprises means for determining a plurality of coefficients of at least three different mathematical functions.

36. A system according to claim 31 wherein said determining means comprises means for determining at least one coefficient from a first mathematical function and at least one other coefficient from a second mathematical function.

* * * * *